(12) United States Patent
Hsieh et al.

(10) Patent No.: US 8,716,512 B2
(45) Date of Patent: May 6, 2014

(54) **PREPARATION AND PURIFICATION OF SUBUNIT VACCINE FOR *NEISSERIA MENINGITIDIS* (NM) GROUP B ISOLATES**

(75) Inventors: Shih-Yang Hsieh, Miaoli County (TW); Pele Choi-Sing Chong, Miaoli County (TW); Chang-Ling Lin, Miaoli County (TW); Chih-Hsiang Leng, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 160 days.

(21) Appl. No.: 13/207,675

(22) Filed: Aug. 11, 2011

(65) Prior Publication Data

US 2012/0041179 A1    Feb. 16, 2012

Related U.S. Application Data

(60) Provisional application No. 61/372,617, filed on Aug. 11, 2010.

(51) Int. Cl.
*C07F 7/00* (2006.01)
(52) U.S. Cl.
USPC .......................................................... 556/425
(58) Field of Classification Search
USPC .......................................................... 556/425
See application file for complete search history.

(56) References Cited

U.S. PATENT DOCUMENTS

| | | | |
|---|---|---|---|
| 6,136,438 A | 10/2000 | Menyes et al. | |
| 7,357,932 B2 | 4/2008 | Yang | |
| 2005/0059766 A1* | 3/2005 | Jones et al. | 524/431 |
| 2005/0196854 A1 | 9/2005 | Konz | |
| 2006/0147177 A1* | 7/2006 | Jing et al. | 385/147 |
| 2007/0087017 A1 | 4/2007 | Olivieri et al. | |
| 2008/0118535 A1 | 5/2008 | Yang | |
| 2009/0176273 A1 | 7/2009 | Leng et al. | |
| 2009/0221499 A1 | 9/2009 | Leng et al. | |
| 2009/0274634 A1 | 11/2009 | Collins et al. | |

FOREIGN PATENT DOCUMENTS

| | | |
|---|---|---|
| GB | 2449306 | 11/2008 |
| WO | 2004/032958 | 4/2004 |
| WO | 2007/070001 | 6/2007 |

OTHER PUBLICATIONS

Sung, JWC, et al. "Biochemical characterizations of *Escherichia coli*-expressed protective antigen Ag473 of *Neisseria meningitides* group B", *Vaccine*, Oct. 23, 2010, vol. 28, pp. 8175-8182.
Chen, HW, et al. "A novel technology for the production of heterologous lipoprotein immunogen in high yield has implications for the field of vaccine design." *Vaccine*, Epub: Jan. 15, 2009, vol. 27, pp. 1400-1409.
Chen, H. et al. "A novel technology for the production of heterogous lapidated immunogens in high yield has implications for the field of vaccine design", *14th International Congress of Immunology*, Kobe, Japan, Aug. 2010, vol. 22, suppl 1, pt 4, PP-069.

* cited by examiner

*Primary Examiner* — Porfirio Nazario Gonzalez
*Assistant Examiner* — Kofi Adzamli
(74) *Attorney, Agent, or Firm* — Cesari and McKenna, LLP

(57) ABSTRACT

A method for preparing and purifying recombinant lipoprotein Ag473 of *Neisseria meningitidis* (NM) group B isolates. The method can be used in large-scale production of vaccines for *Neisseria meningitidis* (NM) group B.

20 Claims, 1 Drawing Sheet

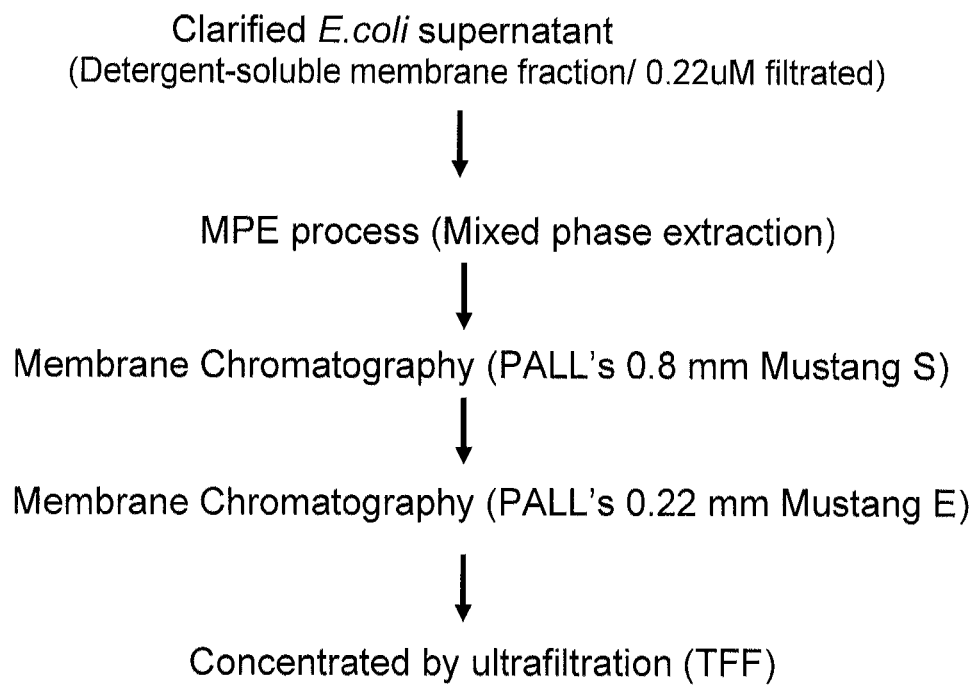

SEQUENCE LISTING

```
<160> NUMBER OF SEQ ID NOS: 1

<210> SEQ ID NO 1
<211> LENGTH: 105
<212> TYPE: PRT
<213> ORGANISM: Neisseria Meningitidis

<400> SEQUENCE: 1

Cys Ser Gln Glu Ala Lys Gln Glu Val Lys Glu Ala Val Gln Ala Val
1               5                   10                  15

Glu Ser Asp Val Lys Asp Thr Ala Ala Ser Ala Ala Glu Ser Ala Ala
            20                  25                  30

Ser Ala Val Glu Glu Ala Lys Asp Gln Val Lys Asp Ala Ala Ala Asp
        35                  40                  45

Ala Lys Ala Ser Ala Glu Glu Ala Val Thr Glu Ala Lys Glu Ala Val
    50                  55                  60

Thr Glu Ala Lys Glu Ala Val Thr Glu Ala Lys Glu Ala Val Thr Glu
65                  70                  75                  80
```

-continued

```
Ala Ala Lys Asp Thr Leu Asn Lys Ala Ala Asp Ala Thr Gln Glu Ala
                85                  90                  95
Ala Asp Lys Met Lys Asp Ala Ala Lys
            100                 105
```

PREPARATION AND PURIFICATION OF SUBUNIT VACCINE FOR *NEISSERIA MENINGITIDIS* (NM) GROUP B ISOLATES

RELATED APPLICATION

This application claims priority of U.S. Provisional Application No. 61/372,617, filed on Aug. 11, 2010. The prior application is incorporated herein by reference in its entirety.

FIELD OF THE INVENTION

The present invention relates to preparing a subunit vaccine for *Neisseria meningitidis* (NM) group B isolates, especially relates to large-scaled production and purification of recombinant Ag473 lipoprotein (rAg473) of *Neisseria meningitidis* (NM) group B from an *E. coli* expression system.

BACKGROUND

To date bacterial meningitis is still a serious threat to global health, accounting for an estimated annual 170,000 deaths worldwide and as many cases of neurological damage especially occurred among infants and youths. *Neisseria meningitidis* (NM) is one of bacteria capable of generating epidemics and will become a major pathogen of human meningitis after the vaccines for *Haemophilus influenza* type b and *Streptococcus pneumonia* are introduced. Traditional polysaccharide-based vaccines for NM serogroups A, C, Y, and W135 have been available since 1970. But a similar approach to develop vaccines for group B is problematic due to potential immunologic cross-reactivity between group B bacterial polysaccharides and human brain glycoproteins. There are several protein-based group B vaccines in the world for regional outbreaks; however, the coverage of such vaccines is limited due to expressions of outer membrane proteins used in these vaccine candidates are very diverse.

After an intensive screening, one lipoprotein, Ag473, was discovered on the surfaces of group B isolates tested. Recombinant lipoprotein Ag473 was demonstrated to be a potential vaccine candidate that is able to elicit efficacy in an animal model. The massive production of rAg473 in *E. coli* for vaccine development and relative use has been achieved by cloning Ag473 gene into an expression vector under the selection of kanamycin to establish the high-expression clones (see, for example, I280247, U.S. Pat. No. 7,357,932, US20080118535, and EP1612218). Since rAg473 is lipidated and anchored in the outer membrane of the bacteria, LPS contamination could be a very serious problem for safety issues in traditional purification process. Therefore, the present invention provides a chromatography technology which successfully removes LPS in recombinant rAg473 production.

SUMMARY

This invention is based on the unexpected discovery that recombinant rAg473 lipoprotein can be successfully purified without LPS contaminant by using a modified chromatography and ultra-filtration technology.

Accordingly, one aspect of this invention features a method of preparing a recombinant lipoprotein from *E. coli* cells, such as a lipoprotein having a molecular weight above 10 kDa and an isoelectric point (pI) below 4.5. The method includes five steps: (1) disrupting cellular membranes of *E. coli* cells expressing an Ag473 protein of *Neisseria meningitidis* (NM) to generate a cell membrane fraction in the presence of a detergent; (2) filtering the cell membrane fraction to generate a filtrate, e.g., by passing a filer membrane with a pore size of 0.22 μm; (3) purifying the filtrate by a purification process to obtain a sample, the purification process includes, in any order, mixed phase chromatography, cation membrane chromatography, and anion membrane chromatography; (4) diafiltrating the sample with a diafiltration membrane (e.g., having a pore size of 10 kD) to generate a preparation; and (5) removing the detergent from the preparation to obtain purified Ag473 protein, e.g., by reversed phase chromatography. Resins, such as a GE's SOURCE 30RPC resin, can be used in the reversed phase chromatography. The resin, loaded with a lipidated rAg473 protein, can be washed with a first solvent containing 40-60% (e.g., 40%) of acetonitrile to remove the residual detergent and then eluted with a second solvent containing 60-90% (e.g., 80%) of acetonitrile to recover the protein.

The detergent used in Step (1) can be a nonionic detergent (e.g., Triton X-100, octyl-b-D-glucopyranoside, NP-40, Triton X-114, and Tween 20), zwitterionic detergent (e.g., CHAPS and CHAPSO), or ionic detergent (SDS and sarcosine). It can have a concentration in the range from 0.01 to 2%, e.g., 0.05 to 1% and 0.1 to 0.5%.

For Step (3), the purification process can include (i) passing the filtrate through a mixed phase chromatography resin to obtain a first elute, the resin being a silica resin modified by silane and activated by acetic acid; (ii) subjecting the first elute to cation membrane chromatography to obtain a second elute; and (iii) subjecting the second elute to anion membrane chromatography to obtain the sample. The silica resin can be obtained by a silane-modification reaction with a ratio of the silica resin to the silane ranging from 2.0 to 3.5 (e.g., 2.5 to 3), calculated based on the dry weight. The mixed phase chromatography can include eluting the resin with a solvent containing NaCl in the range of from 0.25 to 1 M (e.g., 0.5 to 0.75 M). The first elute applied to the cation membrane chromatography can be pre-acidified by adding a solution containing acetic acid to obtain a pH value in the range from 2.5 to 5.0. The second elute applied to the anion membrane chromatography can be pre-basified by adding a solution of NaOH to obtain a pH value in the range from 5.0 to 7.5. The cation membrane chromatography can be carried out with a PALL's 0.8 μm Mustang S membrane. The anion membrane chromatography can be carried out with a PALL's 0.22 μm Mustang E membrane. Step (ii) can be conducted in a phosphate buffer system with a pH value in the range from 3.0 to 4.0. Step (iii) can be conducted in an acetic acid/phosphate buffer system with a pH value above 5.

Another aspect of the invention features a silane-modified silica resin prepared by a process including mixing a silica resin and silane in a solvent, the ratio of the silica resin to the silane being 2.0 to 3.5, calculated based on the dry weight; incubating the mixture so that the silica resin and the silane react with each other to form a silane-modified silica resin; and removing the solvent to obtain a dried silane-modified silica resin. The solvent can be an alcohol, e.g., ethanol and methanol. The duration of the incubation is typically 11 to 16 hours, e.g., 10-14 hours with mixing and then 1-2 hours without mixing. After the incubation, the silane-modified silica resin can be washed with a fresh solvent several times to remove remaining silane. The above-described process can further include activating the silane-modified silica resin by washing it with an acetic acid solution (e.g., 0.1 to 1% acetic acid), removing the acetic acid solution, and washing the activated silane-modified silica resin with a buffer.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is a flow chart of an exemplary 5-step process for purifying recombinant Ag473 lipoprotein (rAg473).

DETAILED DESCRIPTION

The present invention relates to preparing a subunit vaccine for *Neisseria meningitidis* (NM) group B isolates, especially relates to large-scaled production and purification of recombinant Ag473 lipoprotein (rAg473) of *Neisseria meningitidis* (NM) group B from an *E. coli* expression system.

Therefore, in one aspect, the present invention features a method for purification of recombinant lipoprotein Ag473 of *Neisseria meningitidis* (NM) group B in a large-scale *E. coli* expression system, including the steps of: (a) clarifying a supernatant of *E. coli* cells that over-express the lipoprotein using a detergent at certain concentrations that only extracts the rAg473 lipoprotein from cell membrane sufficiently but does not destroy the whole cell structure (that is, the other components of the cells, e.g., cell wall, cytoplasm and genome, are undisrupted and substantially intact); (b) mixed phase chromatographic process of a rAg473 lipoprotein extract in a silica resin made from certain ratios of modifiers (silane) exhibiting good purification application, which is characterized by including an activation process with acetic acid, and elution of the target protein by adding NaCl salt at the concentration of above 0.25 M; (c) cation membrane chromatography characterized by adding acetic acid into the system to acidify the extraction for selectively binding of impurities; (d) anion membrane chromatography with a pH value adjusted to above 5 by adding a solution of NaOH into an acetic acid/phosphate buffer system for removing of contaminants of LPS; (e) diafiltration using a membrane with a pore sizes of different MW cutoff values in the range of 10 to 100 Kds; and optionally (f) reverse phase chromatography to remove the residual detergent.

In one embodiment of the invention, the detergent used in the clarifying step is Triton X-100 at the concentration of 0.05 to 1%. In another embodiment, the mixed phase chromatographic process is carried out using activated silica gel and 0.25 to 1 M NaCl/0.1% Triton X-100/1X PBS (pH7.4) buffers as elution agents.

Further, the present invention provides a large-scale production method of *Neisseria meningitidis* (NM) group B subunit vaccine. The method includes fermentation of *E. coli* host cells (such as C41(DE3)) in a bioreactor using animal component-free media for inducing the expression of rAg473 lipoprotein; extraction of the rAg473 lipoprotein from cell membrane using detergent Triton X-100 at a concentration of 1%; mixed phase chromatographic process of rAg473 lipoprotein extract in a silane-modified silica resin, which is pre-activated with acetic acid; and elution of the protein by adding NaCl at a concentration of above 0.5 N; cation membrane (such as PALL's 0.8 mm Mustang S) chromatography in an acetic acid/phosphate buffer system whose pH value is in the range from 3.0 to 4.0; anion membrane (such as PALL's 0.22 mm Mustang E) chromatography in a buffer system with a pH value above 5; diafiltration using a membrane with a pore size of 10 kDa; and reverse phase chromatography to remove residual detergent using a solvent containing 40 to 60% of acetonitrile and to elute the purified rAg473 protein using another solvent containing 60 to 90% of acetonitrile.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, the steps any mechanism proposed below does not in any way restrict the scope of the claimed invention.

EXAMPLE 1

Preparation of Silica Resin for Purification of rAg473 Lipoprotein

Pharmaceutical grade silicas, PharmPrep® 60 CC (Merck KGaA, Germany, Cat. No. 1.09373.1000) with size distribution in 75 to 200 µm, were modified with correspondent amounts of silane (diethylaminopropyltrimethoxy silane, CAS No. 41051-80-3). A typical anhydrous reaction in ethanol was performed under the condition which the ratio of silica to silane was above 2.5 calculated by their dry weights. This reaction was made of silica particles, 250 g in 10 liter of ethanol (95%), and 100 ml of silane whose density was approximately 0.934 g/ml. The resultant mixture was incubated for a period of 12 hours at room temperature (RT), then replaced with fresh ethanol and kept for another 12 hours with stirring. After repeating this process two times, modified silicas were dried out in an autoclave at 120 and 2 kgf/cm$^2$ for 20 minutes.

For a testing scale, 0.05 g of modified silica gel described above was packed in an Ultrafree-MC tube (Millipore Corp. USA, Cat. No: UFC30HV), washed with 400 µl of dH$_2$O, centrifuged at 12,000 rpm at room temperature for 1 minute. The flow-through liquid was discarded, and the washing and centrifugation steps were repeated once. The silica gel was then washed with 200 µl of 1% acetic acid, centrifuged at 12,000 rpm at room temperature for 1 minute, and the flow-through liquid was discarded. Thereafter, the silica gel was balanced with 400 µl of 0.1% Triton X-100/1X PBS, pH7.4, centrifuged at 12,000 rpm at room temperature fort minute, and the flow-through liquid was discarded. The pre-treating (balancing) step was repeated twice. For a large scale (1,000 g or above), the silica gel was pulled into a chromatographic column, AxiChrom (GE Healthcare Bio-Sciences Corp. USA) equipped with a pump system to conduct the buffer-exchanging.

EXAMPLE 2

Purification of rAg473 Over-expressed in *E. coli* Host Cells

A 5 liter-scale fermentation of *E. coli* C43(DE3) transformed with the Ag473 gene in the plasmid pET9a, using animal component-free media was used to produce rAg473 as a vaccine for preclinical studies. This lipoprotein consists of 105 amino acid residues and N-acyl-S-diacylglyceryl-Cys as its N-terminal amino acid. Its sequence is:

(SEQ ID NO: 1)
CSQEAKQEVKEAVQAVESDVKDTAASAAESAASAVEEAKDQVKDAAADA

KASAEEAVTEAKEAVTEAKEAVTEAKEAVTEAAKDTLNKAADATQEAAD

KMKDAAK.

The fermentation was conducted in an M9 defined medium that supplied with yeast extract. Bacteria cultures were allowed to grow to OD600 of 8 in a 5-L fermentor. Target protein expressions were induced with lactose (the final concentration was 1%). After harvesting cells and disrupting cellular membranes by detergent, a supernatant was obtained by centrifugation at 5,000 rpm, 4° C. for 10 min, filtered through a membrane with 0.22 μm pore size, and subjected to the 5-step purification process as follow. Among the five steps, steps (2), (3), and (4) can be conducted in any order.

A 5-stept purification process was shown in FIG. 1. More specifically, the process included the steps of: (1) disrupting *E. coli* cellular membranes by a detergent (Triton X-100 in this experiment) at certain concentration (such as 1%, preferably) for extracting the rAg473 lipoprotein and clarifying the extract by micro-filtration through a membrane; (2) mixed phase chromatography of the rAg473 lipoprotein extract in a silica resin as prepared in the manner discussed above in Example 1, using 0.5M NaCl/0.1% Triton X-100/1X PBS, pH7.4 as an elution solvent; (3) cation membrane chromatography using a PALL's 0.8 mm Mustang S membrane pretreated in 1% of an acetic acid/0.1% Triton X-100/1X PBS buffer; (4) anion membrane chromatography using a PALL's 0.22 μm Mustang E membrane pretreated in a 0.1% Triton X-100/1X PBS buffer of pH 7.4; and (5) diafiltration through a concentrating membrane with membrane pore sizes of 10 kDa.

The purified fractions after each step were analyzed on SDS-PAGE. The results show that step (2) significantly purified the rAg473 lipoprotein and Steps (3)-(5) further purified it to homogeneity. It was found that the content of endotoxins in the elute of the silica gel chromatography was decreased from more than 1000,000 EU/ml to less than 200,000 EU/ml, suggesting that most of endotoxins had been removed by the silica gel chromatography.

EXAMPLE 3

Evaluation for Immunogenicity of Purified rAg473 Lipoprotein

To evaluate the immunogenic properties of purified rAg473 lipoprotein in vivo, assays were carried out to analyze the magnitude of Ag473-specific antibody responses in mice immunized with various doses (0, 5, 10, 30, and 50 μg/ml) of purified rAg473 lipoprotein. More specifically, groups of 8-12-week old BALB/c mice (n=5) were initially immunized subcutaneously with 0, 5, 10, 30, or 50 μg/ml of purified rAg473 formulated in PBS or with an ALPO$_4$ adjuvant. The same formulation and amount of antigen was used subcutaneously to boost the mice on day 14 after priming. Immune sera were collected by tail vein bleeding at the $2^{nd}$, $3^{rd}$, $4^{th}$, and $6^{th}$ weeks after the booster immunization. Anti-Ag473 antibody titers were determined by ELISA. In brief, microtiter plates were coated with 50 μl of rAg473 solution (2 μg/mL) per well. Bound IgG was detected with horseradish peroxidase-conjugated goat anti-mouse IgG Fc. Color was developed by adding 3,3,5,5-tetramethylbenzidine and the absorbance at 450 nm was measured in an ELISA reader. End-point titers were defined as the serum dilution that resulted in an absorbance value ≥0.2.

The mice immunized with purified rAg473 lipoprotein in PBS or formulated with ALPO$_4$ adjuvant elicited detectable levels of anti-Ag473 IgG antibody responses when compared with the animals immunized with PBS or ALPO$_4$ adjuvant alone (groups of 0 μg/ml rAg473). Also, the mice immunized with purified rAg473 lipoprotein formulated with the ALPO$_4$ adjuvant generated much higher titers of anti-Ag473 antibodies, as compared with those immunized with purified rAg473 lipoprotein in PBS.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. A method of preparing a recombinant lipoprotein from *E. coli* cells, comprising disrupting cellular membranes of *E. coli* cells expressing an Ag473 protein of *Neisseria meningitidis* (NM) to generate a cell membrane fraction in the presence of a detergent;

filtering the cell membrane fraction to generate a filtrate;

purifying the filtrate by a purification process to obtain a sample, the purification process comprising, in any order, mixed phase chromatography in a resin, cation membrane chromatography, and anion membrane chromatography;

diafiltrating the sample with a diafiltration membrane to generate a preparation; and removing the detergent from the preparation to obtain purified Ag473 protein, wherein the resin is an activated silane-modified silica resin prepared by a process comprising: (1) mixing in a solvent a silica resin and silane, the ratio of the silica resin to the silane ranging from about 2.5 to about 3.5, calculated based on dry weight; (2) incubating the mixture so that the silica resin and the silane react with each other to form a silane-modified silica resin; (3) removing the solvent to obtain a dried silane-modified silica resin; (4) activating the silane-modified silica resin by washing it with an acetic acid solution; (5) removing the acetic acid solution; (6) and washing the activated silane-modified silica resin with a buffer.

2. The method of claim 1, wherein said lipoprotein has a molecular weight above 10 kDa and an isoelectric point (pI) below 4.5.

3. The method of claim 1, wherein the detergent has a concentration in the range from 0.05 to 1%, and is selected from the group consisting of Trition X-100,octyl-b-D-glucopyranoside, NP-40,Triton X-114, Tween 20, CHAPS, CHAPSO, SDS, and sarosine.

4. The method of claim 1, wherein the filtering step is conducted by passing a filer membrane with a pore size of 0.22 μm.

5. The method of claim 1, wherein the cation membrane chromatography is carried out with a PALL's 0.8 μm Mustang S membrane.

6. The method of claim 1, wherein the anion membrane chromatography is carried out with a PALL's 0.22 μm Mustang E membrane.

7. The method of claim 1, wherein the purification step is performed by (i) passing the filtrate through the mixed phase chromatography resin to obtain a first elute;

(ii) subjecting the first elute to cation membrane chromatography to obtain a second elute; and (iii) subjecting the second elute to anion membrane chromatography to obtain the sample.

8. The method of claim 7, wherein the mixed phase chromatography in step (i) comprises eluting the resin with a solvent containing NaCl in the range of from 0.25 to 1 M.

9. The method of claim 7, wherein step (ii) is conducted in a phosphate buffer system with a pH value in the range from 3.0 to 4.0.

10. The method of claim 7, wherein the first elute applied to the cation membrane chromatography in step (ii) is pre-acidified by adding a solution containing acetic acid to obtain a pH value in the range from 2.5 to 5.0.

11. The method of claim 7, wherein step (iii) is conducted in an acetic acid/phosphate buffer system with a pH value above 5.

12. The method of claim 7, wherein the second elute applied to the anion membrane chromatography in step (iii) is pre-basified by adding a solution of NaOH to obtain a pH value in the range from 5.0 to 7.5.

13. The method of claim 1, wherein the diafiltration membrane has a pore size of 10 kD.

14. The method of claim 1, wherein the detergent removing step is conducted by reversed phase chromatography comprising washing with a first solvent containing 40% to 60% of acetonitrile to remove the residual detergent, and eluting with a second solvent containing 60% to 90% of acetonitrile to recover the rAg473 protein.

15. A silane-modified silica resin for mixed phase chromatography for purifying a lipoprotein, the resin being prepared by a process comprising mixing in a solvent a silica resin and silane, the ratio of the silica resin to the silane ranging from about 2.5 to about 3.5, calculated based on dry weight;

incubating the mixture so that the silica resin and the silane react with each other to form a silane-modified silica resin; and removing the solvent to obtain a dried silane-modified silica resin.

16. The silane-modified silica resin of claim 15, wherein the process, after the removing step, further comprises activating the silane-modified silica resin by washing it with an acetic acid solution, removing the acetic acid solution, and washing the activated silane-modified silica resin with a buffer.

17. The silane-modified silica resin of claim 15, wherein the ratio of the silica resin to the silane is 2.5.

18. The silane-modified silica resin of claim 15, wherein the ratio of the silica resin to the silane is 3.5.

19. The silane-modified silica resin of claim 15, wherein the silica resin is a pharmaceutical grade silica resin containing silica particles ranging from 75 μm to 200 μm in size.

20. The silane-modified silica resin of claim 15, wherein the acetic acid solution is 0.1% to 1% acetic acid.

* * * * *